United States Patent
Javet et al.

(10) Patent No.: US 6,485,529 B1
(45) Date of Patent: Nov. 26, 2002

(54) AGENT AND METHOD FOR COLORING FIBERS

(75) Inventors: Manuela Javet, Marly (CH); Catherine Mueller, Marly (CH)

(73) Assignee: Wella Aktiengesellschaft, Darmstadt (DE)

( * ) Notice: Subject to any disclaimer, the term of this patent is extended or adjusted under 35 U.S.C. 154(b) by 0 days.

(21) Appl. No.: 09/868,551

(22) PCT Filed: Oct. 12, 2000

(86) PCT No.: PCT/EP00/10049
§ 371 (c)(1), (2), (4) Date: Jun. 19, 2001

(87) PCT Pub. No.: WO01/28507
PCT Pub. Date: Apr. 26, 2001

(30) Foreign Application Priority Data

Oct. 20, 1999 (DE) .......................... 199 50 404

(51) Int. Cl.⁷ ................................. A61K 7/13
(52) U.S. Cl. ...................... 8/405; 8/405; 8/406; 8/409; 8/437; 8/453
(58) Field of Search ............................. 8/405, 406, 409, 8/437, 453

(56) References Cited

U.S. PATENT DOCUMENTS 3,871,818 A * 3/1975 Kinney et al. ................ 8/10.2
4,259,261 A * 3/1981 Bugaut et al. ................ 564/99

FOREIGN PATENT DOCUMENTS

| DE | 197 17 223 A1 | 10/1998 |
| DE | 197 17 224 A1 | 10/1998 |
| DE | 197 17 280 A1 | 10/1998 |
| DE | 197 45 292 A1 | 4/1999 |
| DE | 197 45 356 A | 4/1999 |
| EP | 0 873 744 A | 10/1998 |
| EP | 0 873 745 A | 10/1998 |

OTHER PUBLICATIONS

Long R. and K. Schofield, IN J. Chem. Soc., 3161 (1953).
E. Robert Und E.E. Turner, In J. Chem. Soc., 1832 (1927).
E.A. Fehnel, In J. Org. Chem., 31, 2899 (1966).
C–C. Cheong and S–J Yan, "The Friedlaender Synthesis...", In Org. React., 28, 37 (1982).
Houben–Weyl, "Methoden Der Organischen Chemie . . . ", R. Kreher (HRSG), Georg Thiem–Verlag, BD. E 7A, pp. 553 (1991).

* cited by examiner

*Primary Examiner*—Yogendra N. Gupta
*Assistant Examiner*—Eisa Elhilo
(74) *Attorney, Agent, or Firm*—Michael J. Striker

(57) ABSTRACT

The object of the invention is an agent for coloring fibers, which contains at least one aromatic aldehyde compound, at least one compound of formula (I) or (II) and an alkanolamine,

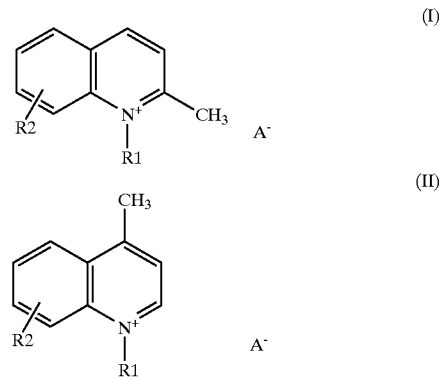

in which R1 represents a C1 to C3 alkyl group, a C1 to C3 alkoxyalkyl group or a C1 to C3 hydroxyalkyl group and R2 represents hydrogen or a hydroxy group, a methoxy group, a halogen atom, an amino group or a dimethylamino group and A⁻ represents an anion, such as chloride, bromide, sulfate, hydrogen sulfate, monomethyl sulfate, acetate, lactate or iodide; a method for coloring fibers using this agent, as well as a multicomponent kit for coloring and, later on, decolorizing fibers.

16 Claims, No Drawings

AGENT AND METHOD FOR COLORING FIBERS

BACKGROUND OF THE INVENTION

The object of the present invention is an agent for coloring fibers, particularly keratin fibers (such as human hair), the agent containing a combination of a 1-alkyl-methylquinolinium salt of formula (I) or (II) and carbonyl compounds, a method for coloring fibers especially keratin fibers, as well as a multi-component kit for coloring and, later on, decolorizing fibers.

Hair coloring agents are divided mainly into the field of oxidizing dyes or tints, depending on the initial color of the hair that is to be dyed and on the desired end result.

Oxidation dyes are outstandingly suitable for covering higher proportions of gray. As a rule, oxidation dyes, used for a proportion of gray up to 50%, are referred to as oxidative tints, whereas the oxidation dyes, used when the proportion of gray exceeds 50% or for "coloring to a brighter color", usually are referred to as so-called oxidative dyes.

Direct dyes are contained mainly in non-oxidative coloring agents (so-called tinting agents). Because of their small size, some direct dyes, such as nitro dyes, can penetrate in the hair and dye it directly, at least in the outer regions. Such tints are very gentle of the hair and usually withstand 6 to 8 washings. Direct dyes, especially nitro dyes, are also frequently used in oxidative coloring agents for producing certain nuances or intensification of the color.

It is well known that colored polymers, oxidatively produced in the hair, generally are resistant to external influences, such as water, shampoo or light. Depending on the coloring technique, they are anchored so firmly, that they remain in the hair until it is cut the next time. However, the use of hydrogen peroxide, especially in an alkaline medium, has a disadvantageous effect on the structure of the hair.

From the German Offenlegungsschrift 197 45 292, the use of a combination of malonaldehyde derivatives, such as malonaldehyde bis-dialkylacetals, and amines or compounds containing an acidic CH group for coloring hair without the addition of oxidizing agent, is known. Likewise, from the state of the art, the use of a combination of certain aldehydes (German Offenlegungsschrift 197 17 280), of certain heterocyclic carbonyl compounds (German Offenlegungsschrift 197 17 223), of certain aminovinyl aldehydes (German Offenlegungsschrift 197 17 224), of certain unsaturated, non-aromatic aldehydes(German Offenlegungsschrift 197 45 356), of certain onium aldehydes or onium ketones) and amines or compounds with an acidic CH group is known for coloring hair without the addition of oxidizing agents. However, these dyes fulfill only partly the requirements that have been set.

Therefore, there continues to be a great need for a dye, which makes intensive as well as gentle colorings possible with a wide range of nuances under mild conditions.

SUMMARY OF THE INVENTION

Surprisingly, it has been found that this objective can be accomplished in an outstanding manner through the use of an agent containing a alkanolamine, at least one carbonyl compound, especially an aromatic (not heterocyclic) aldehyde compound, and at least one compound of formula (I) or (II),

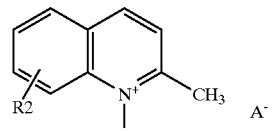

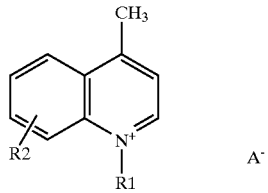

in which R1 represents a C1 to C3 alkyl group, a to C1 to C3 alkoxyalkyl group or a C1 to C3 hydroxyalkyl group and R2 represents hydrogen, a hydroxy group, a methoxy group, a halogen atom, an amino group or a dimethylamino group and A$^-$ represents an anion, such as chloride, bromide, sulfate, hydrogen sulfate, monomethyl sulfate, acetate, lactate or iodide, for coloring fibers, particularly keratin fibers, such as human hair.

The individual components of the inventive coloring agent are kept separate from one another until shortly before their use and mixed only shortly before their use into a ready-for-use coloring agent and then applied on the fibers, which are to be dyed. Several variations are possible here. For example, the compounds of formula (I) and/or (II) can be packaged together with the aldehyde compound and, optionally, direct dyes(=dye carrier composition) and mixed shortly before use with the alkanolamine. It is, however, also possible to produce the inventive coloring agent in the form of a 2-component agent, consisting of a dye carrier composition (a), which contains the compounds of formula (I) and/or (II), as well as the monoalkanolamine and optionally direct dyes, and of a further dye carrier composition (b), which contains the aldehyde compound and, optionally, direct dyes. A further possibility is a 2-component agent, consisting of a dye carrier composition (a), which contains the compounds of formula (I) and/or (II) and optionally direct dyes and of a further dye carrier composition (b), which contains the aldehyde compound, as well as the monoalkanolamine and optionally direct dyes. Of course, it is also possible to produce the three components in the form of a 3-component agent, which consists of a dye carrier composition (a), which contains the compounds of formula (I) and/or (II) and optionally direct dyes, and a further dye carrier composition (b), which contains the aldehyde compound and optionally direct dyes, and a component (c), which contains the alkanolamine.

Of the compounds of formulas (I) and (II), the following are particularly preferred: 1-ethyl-2-methyl-quinolinium iodide, 1-ethyl-2-methyl-quinolinium chloride, 1-ethyl-4-methyl-quinolinium iodide and 1-ethyl-4-methyl-quinolinium chloride.

Some of the compounds of formulas (I) and (II) can be obtained commercially. However, the compounds of formulas (I) and (II) can also be synthesized by conventional methods known from the literature. In this connection, reference is made particularly to the articles of R. Long and K. Schofield in J. Chem. Soc., 3161 (1953), E. Roberts and E. E. Turner in J. Chem. Soc., 1832 (1927), E. A. Fehnel in J. Org. Chem., 31, 2899 (1966) and C.-C. Cheng and S.-J. Yan, "The Friedländer synthesis of quinolines", in Org. React., 28, 37 (1982), in which the synthesis of quinolines, which are not N-alkylated, is described. A method for the alkylation of the quinoline nitrogen is described, for example, in Houben-Weyl, "Methoden der organischen Chemie (Methods of Organic Chemistry), Hetarenes II—Part 1", R. Kreher (editor) Georg Thieme-Verlag, vol. E 7a, page 553 (1991).

The following can be used as aldehyde compounds of component (b): vanillin (4-hydroxy-3-methoxy-benzaldehyde), isovanillin (3-hydroxy-4methoxy-benzaldehyde), 3,4-dihydroxy-benzaldehyde, 4-hydroxy-benzaldehyde, 3,5-dimethoxy-4-hydroxy-benzaldehyde, 4-dimethylamino-benzaldehyde, 4-dimethylamino-cinnamaldehyde, 4-hydroxy-2-methoxy-benzaldehyde, 3,5,-dimethyl-4-hydroxybenzaldehyde, 4-dimethylamino-2-methoxybenzaldehyde, 2-hydroxybenzaldehyde, 4-hydroxy-1-naphthaldehyde, 4-methoxy-1-naphthaldehyde, 4-dimethylamino-1-naphthaldehyde, 4'-hydroxy-biphenyl-1-carbaldehyde, 2-hydroxy-3-methoxybenzaldehyde, 2,4-dihydroxy-benzaldehyde, 3,4-dihydroxy-benzaldehyde, 2,5-dihydroxybenzaldehyde, 2,3,4-trihydroxybenzaldehyde, 3,4,5-trihydroxybenzaldehyde, 2,4,6-trihydroxybenzaldehyde, 2,4-dimethoxybenz-aldehyde, 2,3-dimethoxy-benzaldehyde, 2,5-dimethoxybenzaldehyde, 3,5-dimethoxy-benzaldehyde, 3,4-dimethoxy-benzaldehyde, benzene-1,4-dicarbaldehyde, 4-ethoxy-benzaldehyde, 2-methyl-1,4-naphthoquinone, 4-carboxybenzaldehyde, 4-hydroxy-3-methoxy-cinnamaldehyde, 3,5-dimethoxy-4-hydroxy-cinnamaldehyde, 3-methoxy-4-(1-pyrrolidinyl)-benzaldehyde, 4-diethylamino-3-methoxy-benzaldehyde, 1,2-phthaldialdehyde, 4-dibutylamino-benzaldehyde, 4-diethylamino-2-hydroxybenzaldehyde, 3,4-dimethoxy-5-hydroxy-benzaldehyde, 5-(4-(diethylamino)phenyl)-2,4-pentadienal, 2-methoxy-1-naphthaldehyde, 3-ethoxy-4-hydroxybenzaldehyde, 2-nitrobenzaldehyde, 3-nitrobenzaldehyde and the 4-nitrobenzaldehyde.

As alkanolamine, monoethanolamine, isopropanolamine and diisopropanolamine come into consideration, isopropanolamine and especially monoethanolamine being preferred. The alkanolamine is added in an amount, which is sufficient in order to adjust the pH of the inventive agent to the desired value.

The compounds of formula (I) and/or (II) and the aldehyde compounds are contained in the respective dye carrier composition in a total amount of about 0.02 to 20 percent by weight and preferably of 0.2 to 10 percent by weight. In the ready-for-use coloring agent, obtained by mixing the individual components, the compounds of formula (I) and/or (II) and the aldehyde compound are contained in each case in a total amount of about 0.01 to 10 percent by weight and preferably of 0.1 to 5 percent by weight.

Furthermore, the inventive coloring agent optionally may contain further, conventional, physiologically safe, direct dyes from the group of nitro dyes, azo dyes, quinone dyes and triphenylmethane dyes, such as 1,4-bis[(2-hydroxy-ethyl)amino]-2-nitrobenzene, 1-(2-hydroxyethyl)amino-2-nitro-4-[di(2-hydroxyethyl)amino]-benzene (HC Blue No. 2), 1-amino-3-methyl-4-[(2-hydroxyethyl)amino]-6-nitrobenze (HC) Violet No. 1), 4-[ethyl-(2-hydroxy-ethyl)amino]-1-[(2-hydroxyethyl)amino]-2-nitrobenzene hydrochloride (HC Blue No. 12), 4-[di(2-hydroxyethyl)amino-]1-[(2-methoxyethyl)amino]-2-nitrobenzene (HC Blue No. 11), 1-[(2,3-dihydroxypropyl)amino]-4-[methyl-(2-hydroxyethyl)amino]-2-nitrobenzene (HC Blue No. 10), 1-[(2,3-dihydroxypropyl)amino]-4-[ethyl-(2-hydroxyethyl)amino]-2-nitrobenzene hydrochloride (HC Blue No. 9), 1-(3-hydroxypropylamino)-4-[di(2-hydroxyethyl)amino]-2-nitrobenzene (HC Violet No. 2), 1-methylamino-4-[methyl-(2,3-dihydroxypropyl)amino]-2-nitrobenzene (HC Blue No. 6), 2-((4-amino-2-nitrophenyl)amino)-5-dimethylamino-benzoic acid (HC Blue No. 13), 1-(2-aminoethylamino)-4-[di(2-hydroxyethyl)amino]-2-nitrobenzene, 1-amino-4-[(2-hydroxyethyl)-amino]-2-nitrobenzene (HC Red No. 7), 2-amino-4,6-dinitro-phenol, 4-amino-2-nitro-diphenylamine (HC Red No. 1), 1-amino-4-[di(2-hydroxyethyl)amino]-2-nitrobenzene hydrochloride (HC Red No. 13), 1-amino-5-chloro-4-[(2-hydroxyethyl)amino]-2-nitrobenzene, 4-amino-1-[(2-hydroxyethyl)amino]-2-nitrobenzene (HC Red No. 3), 4-((2-hydroxyethyl) methylamino)-1-(methylamino)-2-nitrobenzene, 1-amino-4-((2,3-dihydroxypropyl)amino)-5-methyl-2-nitrobenzene, 1-amino-4-(methylamino)-2-nitrobenzene, 4-amino-2-nitro-1-((prop-2-en-1-yl)amino)-benzene, 4-amino-3-nitrophenol, 4-[(2-hydroxyethyl)amino]-3-nitrophenol-1-[(2-aminoethyl)amino]-4-(2-hydroxyethoxy)-2-nitrobenzene (HC Orange No. 2), 4-(2,3-dihydroxypropoxy)-1-[(2-hydroxyethyl)amino]-2-nitrobenzene (HC Orange No. 3), 1-amino-5-chloro-4-[(2,3-dihydroxy-propyl)amino]-2-nitrobenzene (HC Red No. 10), 5-chloro-1,4-[di(2,3-dihydroxypropyl)amino]-2-nitrobenzene (HC Red No. 11), 2-[(2-hydroxy -ethyl)amino]-4,6-dinitrophenol, 4-ethylamino-3-nitrobenzoic acid, 2-[(4-amino-2nitrophenyl)amino]-benzoic acid, 2-chloro-6-ethylamino-4-nitrophenol, 2-amino-6-chloro-4-nitrophenol, 4-[(3-hydroxypropyl)amino]-3-nitrophenol, 2,5-diamino-6-nitropyridine, 6-amino-3-((2-hydroxyethyl)-amino-2-nitropyridine, 3-amino-6-((2-hydroxyethyl)amino)-2-nitropyridine, 3-amino-6-(ethylamino)-2-nitropyridine, 3-((2-hydroxyethyl)amino)-6-(methylamino)-2-nitropyridine, 3-amino-6-(methylamino)-2-nitropyridine, 6-(ethylamino)-3-((2-hydroxyethyl)amino)-2-nitropyridine, 1,2,3,4tetrahydro-6-nitroquinoxaline, 7-amino-3,4-dihydro-6-nitro-2H-1,4-benzoxazine (HC Red No. 14),1-amino-2-[(2-hydroxyethyl)amino]-5-nitrobenzene (HC Yellow No. 5), 1-(2-hydroxyethoxy)-2-[(2-hydroxyethyl)-amino]-5-nitrobenzene (HC Yellow No. 4), 1-[(2-hydroxyethyl) amino]-2-nitrobenzene (HC Yellow No. 2), 2-(di(2-hydroxyethyl)amino)-5-nitrophenol, 2-[(2-hydroxyethyl) amino]-1-methoxy-5-nitrobenzene, 2-amino-3-nitrophenol, 1-(2-hydroxyethoxy)-3-methylamino-4-nitrobenzene, 2,3-(dihydroxypropoxy)-3-methylamino-4-nitrobenzene, 2-[(2-hydroxyethyl)amino]-5-nitrophenol (HC Yellow No. 11), 3-[(2-aminoethyl)amino]-1-methoxy-4-nitrobenzene hydrochloride (HC Yellow No. 9), 1-[(2-ureidoethyl)-amino]-4-nitrobenzene, 4-[(2,3-dihydroxypropyl)-amino]-3-nitro-1-trifluoromethyl-benzene (HC Yellow No. 6), 1-chloro-2,4-bis[(2-hydroxyethyl)amino]-5-nitrobenzene (HC Yellow No. 10), 1-amino-4-((2-aminoethyl)-amino)-5-methyl-2-nitrobenzene, 4-[(2-hydroxyethyl)amino]-3-nitro-1-methylbenzene, 1-chloro-4-[(2-hydroxyethyl)amino]-3-nitrobenzene (HC Yellow No. 12), 4-[(2-hydroxyethyl) amino]-3-nitro-1-trifluoromethyl-benzene (HC Yellow No. 13), 4-[(2-hydroxyethyl)amino]-3-nitrobenzonitrile (HC Yellow No. 14), 4-[(2-hydroxyethyl)amino]-3-nitrobenzamide (HC Yellow No. 15), 3-((2-hydroxyethyl) amino)-4-methyl-1-nitrobenzene, 4-chloro-3-((2-hydroxyethyl)amino)-1-nitrobenzene, 1,4-di[(2,3-dihydroxy-propyl)amino]-9,10-anthraquinone, 1-[(2-hydroxyethyl)amino]-4-methyl-amino-9,10-anthraquinone (CI61505, Disperse Blue No. 3), 2-[(2-amino-ethyl)amino]-9,10-anthraquinone (HC Orange No. 5), 1-hydroxy-4-[(4-methyl-2-sulfophenyl)amino]-9,10-anthraquinone, 1-[(3-aminopropyl)-amino]-4-methylamino-9,10-anthraquinone (HC Blue No. 8), 1-[(3-amino-propyl)amino]9,10- anthraquinone (HC Red No. 8), 1,4-diamino-2-methoxy-9,10-anthraquinone (CI62015, Disperse Red No. 11, Solvent Violet No. 26), 1,4-dihydroxy-5,8-bis[(2-hydroxyethyl)amino]-9,10-anthraquinone (CI62500, Disperse Blue No. 7, Solvent Blue No. 69), 9-(dimethylamino)-benzo[a]phenoxazin-7-ium chloride (CI51175; Basic Blue No. 6), di[4-(diethylamino)phenyl][4-(ethylamino)naphthyl] carbenium chloride (CI42595; Basic Blue No. 7), di-(4-(dimethylamino)phenyl)-(4-(methyl-phenylamino) naphthalene-1-yl)carbenium chloride (CI42563; Basic Blue No. 8), 3,7-di(dimethylamino)phenothiazin-5-ium chloride (CI52015; Basic Blue No. 9), di[4-(dimethylamino)phenyl][4-(phenylamino)naphthyl]-carbenium chloride (CI44045; Basic Blue No. 26), 2-[(4-ethyl(2-hydroxy-ethyl)amino) phenyl)azo]-6-methoxy-3-methyl-benzothiazolium-methyl sulfate (CI11154; Basic Blue No. 41), 8-amino-2-bromo-5-hydroxy-4-imino-6-[(3-(trimethylammonio)phenyl)amino]-1(4H)-naphthalinone chloride (CI56059; Basic Blue No. 99), bis[4-(dimethylamino)phenyl][4-(methyl-amino) phenyl]carbenium chloride (CI42535; Basic Violet No. 1), tris[4-(dimethylamino)phenyl]carbenium chloride (CI42555; Basic Violet No. 3), 2-[3,6-(diethylamino) dibenzopyranium-9-yl]-benzyl chloride (CI45170; Basic Violet No. 10), di(4-aminophenyl)(4-amino-3-methyl-phenyl)carbenium chloride (CI42510; Basic Violet No. 14), 1,3-bis[(2,4-diamino-5-methylphenyl)azo]-3-methylbenzene (CI21010; Basic Brown No. 4), 1-[(4-aminophenyl)azo]-7-(trimethylammonio)-2-naphthol chloride (CI 12250; Basic Brown No. 16), 1-[(4-amino-2-nitrophenyl)azo]-7-(trimethylammonio)-2-naphthol chloride (Basic Brown No. 17), 1-[(4-amino-3-nitrophenyl)azo]-7-(trimethylamino)-2-naphthol chloride (CI12251; Basic Brown No. 17) 3,7-diamino-2,8dimethyl-5-phenyl-phenazinium chloride (CI50240; Basic Red No. 2), 1,4-dimethyl-5-[(4-(dimethylamino)phenyl)azo]-1,2,4-triazolium chloride (CI1105 5; Basic Red No. 22), 2-hydroxy-1-[(2-methoxyphenyl)azo]-7-(trimethylammonio)-naphthalene chloride (CI12245; Basic Red No. 76), 2-[2-((2,4-dimethoxy-phenyl)amino)ethenyl]-1,3,3-trimethyl-3H-indol-1-ium chloride (C148055; Basic Yellow No. 11), 3-methyl-1-phenyl-4-[(3-(trimethylammonio)-phenyl)azo]-pyrazol-5-one chloride (CI12719; Basic Yellow No. 57), di(4-(dimethylamino)phenyl)iminomethane hydrochloride (C 141000; Basic Yellow No. 2), bis[4-(diethylamino)phenyl]phenylcarbenium hydrogen sulfate (1:1) (CI42040; Basic Green No. 1), di(4-(dimethylamino)-phenyl)-phenylmethanol (CI42000; Basic Green No. 4), 1-[di(2-hydroxy-ethyl)amino]-3-methyl-4-[(4-nitrophenyl) azo]-benzene (CI11210, Disperse Red No. 17), 4-[(4-aminophenyl)azo]-1-[di(2-hydroxyethyl)amino]-3-methylbenzene (HC Yellow No. 7), -2,6-diamino-3-[(pyridine-3-yl)azo]-pyridine, 2-((4-(acetylamino)phenyl) azo)-4-methylphenol (CI11855; Disperse Yellow No. 3), 6-hydroxy-5-[(4-sulfophenyl)azo]-2-naphthalene sulfonic acid disodium salt (CI15985; Food Yellow No. 3; FD&C Yellow No. 6), 2,4-dinitro-1-naphthol-7-sulfonic acid disodium salt (CI10316; Acid Yellow No. 1; Food Yellow No. 1), 2-(indane-1,3-dion-2-yl)quinoline-x,x-sulfonic acid (mixture of mono- and disulfonic acids) (CI47005; D&C Yellow No. 10; Food Yellow No. 13; Acid Yellow No. 3), 5-hydroxy-1-(4-sulfophenyl)-4-[(4-sulfophenyl)azo] pyrazol-3-carboxylic acid trisodium salt (CI19140; Food Yellow No. 4; Acid Yellow No. 23), 9-(2-carboxyphenyl)-6-hydroxy-3H-xanthene-3-one (CI45350; Acid Yellow No. 73; D&C Yellow No. 8),4-((4-amino-3-sulfophenyl)azo) benzene sulfonic acid disodium salt (CI13015, Acid Yellow No. 9), 5-[(2,4-dinitrophenyl)amino]-2-phenylamino- benzenesulfonic acid sodium salt (CI10385; Acid Orange No. 3), 4-[(2,4-dihydroxyphenyl)azo]-benzenesulfonic acid monosodium salt (CI14270; Acid Orange No. 6), 4-[(2-hydroxynaphth-1-yl)azo]-benzenesulfonic acid sodium salt (CI15510; Acid Orange No. 7), 4-[(2,4-dihydroxy -3-[(2,4-dimethylphenyl)azo]phenyl)azo]-benzenesulfonic acid sodium salt (CI20170; Acid Orange No. 24), 4-hydroxy-3-[(4-sulfonaphth-1-yl)azo]-1-naphthalene-sulfonic acid disodium salt (CI14720; Acid Red No. 14), 6-hydroxy-5-[(4-sulfonaphth-1-yl)azo]-2,4-naphthalene-disulfonic acid trisodium salt (CI16255; Ponceau 4R; Acid Red No. 18), 3-hydroxy-4-[(4-sulfonaphth-1-yl)azo]-2,7-naphthalene-disulfonic acid trisodium salt (CI16185; Acid Red No. 27), 8-amino-1-hydroxy-2-(phenylazo)-3,6-naphthalene-disulfonic acid disodium salt (CI17200; Acid Red No. 33), 5-(acetylamino)-4-hydroxy-3-[(2-methylphenyl)azo]-2,7-naphthalene-disulfonic acid disodium salt (CI18065; Acid Red No. 35), 2-(3-hydroxy-2,4,5,7-tetraiodo-dibenzopyrane-6-one-9-yl)-benzoic acid disodium salt (CI45430; Acid Red No. 51), N-[6-(diethylamino)-9-(2,4-disulfophenyl)-3H-xanthene-3-ylidene]-N-ethyl-ethane ammonium hydroxide, internal salt, sodium salt (CI45100; Acid Red No. 52), 8-[(4-(phenylazo)phenyl)azo]-7-naphthol-1,3-disulfonic acid disodium salt (CI27290; Acid Red No. 73), 2',4',5',7'-tetrabromo-3',6'-dihydroxyspiro [isobenzofuran-1(3H),9'-[9H]xanthene]-3-one-disodium salt (CI45380; Acid Red No. 87), 2',4',5',7',-tetrabromo-4,5,6,7-tetrachloro-3',6'-dihydroxyspiro[isobenzofuran-1(3H),9' [9H]xanthene]-3-one-disodium salt CI145410; Acid Red No. 92), 3',6'-dihydroxy-4',5'diiodospiro-[isobenzofuran-1 (3H),9'(9H)-xanthene]-3-one-disodium salt (CI45425; Acid Red No. 95), 2-hydroxy-3-((2-hydroxynaphth-1-yl)azo)-5-nitrobenzene-sulfonic acid monosodium salt (CI15685; Acid Red No. 184), (2-sulfophenyl)di[4-(ethyl((4-sulfophenyl) methyl)amino)phenyl]-carbenium-disodium salt, betaine (CI42090; Acid Blue No. 9; FD&C Blue No. 1), 1,4-bis[(2-sulfo-4-methylphenyl)amino]-9,10-anthraquinone-disodium salt (CI61570; Acid Green No. 25), bis[4-(dimethylamino)-phenyl]-(3,7-disulfo-2-hydroxynaphth-1-yl)carbenium internal salt, monosodium salt (CI44090; Food Green No. 4; Acid Green No. 50), bis[4-(diethylamino) phenyl](2,4-disulfophenyl)carbenium internal salt, sodium salt (2:1) (CI42045; Food Blue No. 3; Acid Blue No. 1), bis[4-(diethylamino)phenyl](5-hydroxy-2,4-disulfophenyl) carbenium internal salt, calcium salt (2: 1) (CI42051; Acid Blue No. 3), 1-amino-4-(cyclohexylamino)-9,10-anthraquinone-2-sulfonic acid sodium salt (CI62045; Acid Blue No. 62), 2-(1,3-dihydro-3-oxo-5-sulfo-2H-indol-2-ylidene)-2,3-dihydro-3-oxo-1H-indol-5-sulfonic acid disodium salt (CI73015; Acid Blue No. 74), 9-(2-carboxyphenyl)-3-[(2-methylphenyl)amino]-6-[(2-methyl-4-sulfophenyl)amino]xanthylium internal salt monosodium salt (CI45190; Acid Violet No. 9), 1-hydroxy-4-[(4-methyl-2-sulfophenyl)-amino]-9,10-anthraquinone sodium salt (CI60730; D&C Violet No. 2; Acid Violet No. 43), bis[3-nitro-4-[(4-phenylamino)-3-sulfo-phenylamino]-phenyl]-sulfone (CI10410; Acid Brown No. 13), 5-amino-4-hydroxy-6-[(4-nitrophenyl)azo]-3-(phenylazo)-2,7-naphthalene-disulfonic acid disodium salt (CI20470; Acid Black No. 1), 3-hydroxy-4-[(2-hydroxynaphth-1-yl)azo]-7-nitro-1-naphthalene-sulfonic acid chromium complex (3:2) (CI15711; Acid Black No. 52), 3-[(2,4-dimethyl-5-sulfophenyl)azo]-4-hydroxy-1-naphthalene -sulfonic acid disodium salt (CI14700; Food Red No. 1; Ponceau SX; FD&C Red No. 4), 4-(acetylamino)-5-hydroxy-6-[(7-sulfo-4-[(4-sulfophenyl)azo[naphth-1-yl)azo]1,7-naphthalenedisulfonic acid tetrasodium salt (CI28440; Food Black No. 1), 3-hydroxy-4-(3-methyl-5-oxo-1-phenyl-4,5-dihydro-1H-pyrazol-4-ylazo)-naphthalene -1-sulfonic acid sodium salt, chromium complex (Acid Red No. 195), 4-((5-((2-hydroxy-ethyl)amino-1-methyl-1H-pyrazol-4-yl) imino)-4,5-dihydro-5-((2-hydroxy ethyl)imino)-1-methyl-1H-pyrazol monosulfate, 5-hydroxy-1,4-naphthoquinone (CI75500, Natural Brown No. 7), 2-hydroxy-1,4-naphthoquinone (CI75480, Natural Orange No. 6) and 1,2-dihydroxy-2-(1,3-dihydro-3-oxo-2H-indol-2-ylidene)-3H-indol-3-one (CI73000).

The direct dyes may be contained in the dye carrier composition in each case in a total amount of about 0.02 to 20 percent by weight and preferably of 0.2 to 10 percent by weight. The total amount of direct dyes in the ready-for-use coloring agent, obtained by mixing the individual components, is about 0.01 to 5 percent by weight and preferably 0.1 to 10 percent by weight.

The dye carrier compositions, like the ready-for-use coloring agents, independently of one another, are present in the form of a solution, especially of an aqueous or aqueous alcoholic solution, a cream, an emulsion or an aerosol foam.

The dye carrier compositions may contain all materials, customary and known for such preparations, such as solvents, like water, low molecular weight aliphatic alcohols, such as ethanol, n-propanol and isopropanol or glycols, such as glycerin and 1,2-dihydroxypropane, furthermore, wetting agents or emulsifiers from the classes of anionic, cationic, amphoteric or nonionic, surface active substances, such as fatty alcohol sulfates, ethoxylated fatty alcohol sulfates, alkyl sulfonates, alkyl benzene sulfonates, alkyltrimethylammonium salts, alkyl betaines, ethoxylated fatty alcohols, ethoxylated nonylphenols, fatty acid alkanolamides, ethoxylated fatty alcohols, ethoxylated nonylphenols, fatty acid alkanolamides, ethoxylated esters of fatty acids, furthermore thickeners, such as higher molecular weight fatty alcohols, starch or cellulose derivatives, perfumes, hair pre-treatment agents, conditioners, hair swelling agents, preservatives, furthermore Vaseline, paraffin oil and fatty acids, as well as care materials, such as cationic resins, lanolin derivatives, cholesterol, pantothenic acid and betaine. The aforementioned materials are used in amounts customary for such purposes. For example, the wetting agents and emulsifiers are used in concentrations of about 0.5 to 30 percent by weight (in each case based on the individual dye carrier composition), the thickeners in an amount of about 0.1 to 25 percent by weight (in each case based on the individual dye carrier compositions) and the care materials in a concentration of about 0.1 to 5.0 percent by weight (in each case based on the individual dye carrier compositions).

The pH of the ready-for-use coloring agent is adjusted by mixing the individual components and is about 3 to 11, preferably 8 to 11 and especially 9.5 to 11. A particularly good shelf life of the dye carrier compositions results when the dye carrier composition (a), containing the compounds of formula (I) and/or (II) and optionally direct dyes, has an acidic pH of about 1.5 to 6.8 and the dye carrier composition (b), containing the aldehyde compound as well as the monoalkanolamine and optionally direct dyes has an alkaline pH of about 9 to 13. If the inventive coloring agent is produced in the form of a 2-component agent consisting of a dye carrier composition (a), which contains the compounds of formula (I) and/or (II) as well as the monoalkonolamine and optionally direct dyes, and a further dye carrier composition (b), which contains the aldehyde compound and optionally direct dyes, the dye carrier composition (a) has an alkaline pH of about 9 to 13 and the dye carrier composition (b) has an acidic pH of about 1.5 to 6.8.

To adjust the pH to a value suitable for coloring, further alkalizing agents, such as alkylamines, alkali or alkaline earth hydroxides or ammonium hydroxide and alkali carbonates or ammonium carbonates, or acids such as lactic acid, acetic acid, tartaric acid, phosphoric acid, hydrochloric acid, citric acid, ascorbic acid and boric acid, can be used if necessary, in addition to the alkanolamine.

The individual components are mixed immediately before use and applied on the fibers, such as hair. Depending on the depth of color desired, the mixture is allowed to act for 5 to 60 minutes and preferably 15 to 30 minutes, at a temperature of 20° to 50° C. and especially at 30° to 40° C. Subsequently, the fibers are rinsed with water, optionally washed with a shampoo and then dried.

The compounds of formula (I) and/or (II) and the aldehyde compound are generally used in an equimolar ratio in the ready-for-use coloring agent. Depending on the shade of color desired, one or more of the compounds of formula (I) and/or (II) can be mixed with one or more aldehyde compounds, as a result of which a broad spectrum of different nuances can be produced.

The inventive coloring agents produce an excellent coloration of keratin fibers, especially of human hair, but also of wool or silk, in yellow to blue and green color shades.

Surprisingly, these colorations can be decolorized rapidly, gently and completely once again by reducing agents.

A further object of the present invention therefore is a multi-component kit for coloring and later on decolorizing fibers, such as wool, silk, cotton or hair and particularly human hair, wherein the kit contains the inventive coloring agent A and a decolorizing component B, component B, as decolorizing agent, containing at least a sulfite and/or hydrogen sulfite, such as ammonium hydrogen sulfite, ammonium sulfite, alkali sulfite or alkaline earth sulfite, particularly sodium sulfite or ammonium hydrogen sulfite, and/or thioglycolic acid or its salts and having a pH of 4 to 8, the use of thioglycolic acid or its salts at a pH of 7 to 8 being preferred.

The total amount of sulfite, hydrogen sulfite and thioglycolic acid in component B is about 0.1 to 10 percent by weight and preferably 2 to 5 percent by weight.

The agent for decolorizing the fibers, dyed with the coloring agent A (referred to in the following as "decolorizing agent") may be an aqueous or aqueous alcoholic solution, a gel, a cream, an emulsion or a foam. The decolorizing agent may be in the form of a one-component preparation as well as in the form of a multicomponent preparation. The decolorizing agent may also be produced in the form of a powder or (for protection against the formation of dust), of a tablet or effervescent tablet or of a granulate. From this, the decolorizing agent is produced before use with cold water or warm water, optionally with the addition of one or more of the following auxiliary agents. It is, however, also possible that these auxiliary agents (if they are present in solid form), are already contained in the decolorizing powder or granulate or the tablet. Dust formation can additionally be reduced by wetting the powder with oils or waxes.

The decolorizing agent may contain additional auxiliary agents, such as solvents like water, low molecular weight aliphatic alcohols, such as ethanol, n-propanol and isopropanol, glycol ethers or glycols, such as glycerin and particularly 1,2-dihydroxypropane, furthermore wetting agents or emulsifiers from the classes of anionic, cationic, amphoteric or nonionic surface active substances, such as fatty alcohol sulfates, ethoxylated fatty alcohol sulfates, alkyl sulfonates, alkylbenzenesulfonates, alkyltrimethylammonium salts, alkyl betaines, ethoxylated fatty alcohols, ethoxylated nonylphenols, fatty acid alkanolamides, ethoxylated fatty alcohols, ethoxylated nonylphenols, fatty acid alkanolamides, ethoxylated esters of fatty acids, furthermore thickeners, such as fatty alcohols, starch or cellulose derivatives, perfumes, hair pre-treatment agents, conditioners, hair swelling agents, preservatives, Vaseline, paraffin oil and fatty acids, as well as care materials, such as cationic resins, lanolin derivatives, cholesterol, pantothenic acid and betaine.

The pH of the decolorizing agent is about 4 to 8 and, in particular, about 3 to 7.5. If necessary, the pH can be adjusted to the desired value by the addition of suitable acids, such as a-hydroxycarboxylic acids, such as lactic acid, tartaric acid, citric acid or malic acid, phosphoric acid, acetic acid, glycolic acid, salicylic acid, glutathione or gluconic acid lactone, or by the addition of alkalizing agents, such as alkanolamines, alkylamines, alkali hydroxides, ammonium hydroxide, alkali carbonates, ammonium carbonates or alkali phosphates.

The period of action of the decolorizing agent depends on the coloring that is to be decolorized and on the temperature (about 20° to 50° C.) and is 5 to 60 minutes and, in particular 15 to 30 minutes. The decolorizing process can be accelerated by supplying heat. At the end of the period of action of the decolorizing agent, the hair is rinsed with water and optionally washed with a shampoo.

The following examples are intended to illustrate the object of the invention in greater detail without limiting it to these examples.

EXAMPLES

Examples 1 to 10

Hair Dyeing Agent
Component (a) Containing the Compound of Formula (I) or (II)

| Compound of Formula (I) or (II) | Quantitative data according to Table 1 |
|---|---|
| 6-O-palmitoyl-L-ascorbic acid | 0.30 g |
| cetyl stearyl alcohol | 12.00 g |
| lauryl ether sulfate, 28% aqueous solution | 10.00 g |
| ethanol | 23.0 g |
| water, fully desalinated | ad 100.0 g |

The cetyl stearyl alcohol is melted at 80° C. The lauryl ether sulfate is heated with 95% of the water to 80° C. and added to the molten cetyl stearyl alcohol and stirred until a cream results. The compound (I) or (II), mixed with remaining water and the alcohol and the 6-O-palmitoyl-L-ascorbic acid, is added at room temperature. The pH of the cream is adjusted with monoethanolamine to a value of 12.0.
Aldehyde-Containing Component (b)

| Aldehyde compound | Quantitative data according to Table 1 |
|---|---|
| direct dye | Quantitative data according to Table 1 |
| cetyl stearyl alcohol | 12.00 g |
| lauryl ether sulfate, 28% aqueous solution | 10.00 g |
| 6-O-palmitoyl-L-ascorbic acid | 0.30 g |
| ethanol | 23.0 g |
| water, fully desalinated | ad 100.0 g |

The cetyl stearyl alcohol is melted at 80° C. The lauryl ether sulfate is heated with 95% of the water to 80° C. and added to the molten stearyl alcohol and stirred until a cream results. The aldehyde compound, mixed with the remaining water and the alcohol and the 6-O-palmitoyl-L-ascorbic acid, is added at room temperature. The pH of the cream is adjusted to a value of 4.0 with 10% aqueous lactic acid.

Component (a) (5 g) is mixed with 5 g of component (b). The pH of the finished mixture is adjusted optionally with monoethanolamine to 10.5. The ready-for-use hair coloring agent obtained is applied on a strand of hair and distributed uniformly with a brush. After a period of action of 30 minutes at 40° C., the hair is washed with a shampoo, subsequently rinsed with lukewarm water and then dried.

The colorings obtained are summarized in the following Table 1.

Examples 11 to 13

Hair Dyeing Agent
Component (a) Containing a Compound of Formula (I)

| Compound of Formula (I) | Quantitative data according to Table 2 |
|---|---|
| cetyl stearyl alcohol | 12.0 g |
| lauryl ether sulfate, 28% aqueous solution | 10.0 g |
| ethanol | 25.0 g |
| water, fully desalinated | ad 100.0 g |

The cetyl stearyl alcohol is melted at 80° C. The lauryl ether sulfate is heated with 95% of the water to 80° C. and added to the molten stearyl alcohol and stirred until a cream results. The compound of formula (I), mixed with the remaining water and the alcohol, is added at room temperature.
Aldehyde-Containing Component (b)

| Aldehyde compound | Quantitative data according to table 2 |
|---|---|
| cetyl stearyl alcohol | 12.0 g |
| lauryl ether sulfate, 28% aqueous solution | 10.0 g |
| ethanol | 25.0 g |
| water, fully desalinated | ad 100.0 g |

The cetyl stearyl alcohol is melted at 80° C. The lauryl ether sulfate is heated with 95% of the water to 80° C. and added to the molten stearyl alcohol and stirred until a cream results. The aldehyde, mixed with the remaining water and the alcohol, is added at room temperature. The pH of the cream is adjusted with monoethanolamine to a value of 10.2.

Component (a) (5 g) is mixed with 5 g of component (b). The pH of the finished mixture is adjusted optionally with monoethanolamine to a value of 10.0. The ready-for-use hair coloring agent obtained is applied on a strand of hair and distributed uniformly with a brush. After a period of action of 30 minutes at 40° C., the hair is washed with a shampoo, subsequently rinsed with lukewarm water and then dried.

The colorings obtained are summarized in the following Table 2.

Examples 14 to 16

Hair Dyeing Agent

Component (a) Containing a Compound of Formula (II)

| Compound of Formula (II) | Quantitative data according to Table 3 |
|---|---|
| cetyl stearyl alcohol | 12.00 g |
| lauryl ether sulfate, 28% aqueous solution | 10.00 g |
| water, fully desalinated | ad 100.0 g |

The cetyl stearyl alcohol is melted at 80° C. The lauryl ether sulfate is heated with 95% of the water to 80° C. and added to the molten stearyl alcohol and stirred until a cream results. The compound of formula (II), mixed with the remaining water, is added at room temperature.

Aldehyde-Containing Component (b)

| Aldehyde compound | Quantitative data according to Table 3 |
|---|---|
| cetyl stearyl alcohol | 12.0 g |
| lauryl ether sulfate, 28% aqueous solution | 10.0 g |
| water, fully desalinated | ad 100.0 g |

The cetyl stearyl alcohol is melted at 80° C. The lauryl ether sulfate is heated with 95% of the water to 80° C. and added to the molten stearyl alcohol and stirred until a cream results. The aldehyde, mixed with the remaining water, is added at room temperature. The pH of the cream is adjusted with monoethanolamine to a value of 10.2.

Component (a) (5 g) is mixed with 5 g of component (b). The pH of the finished mixture is adjusted optionally with monoethanolamine to a value of 10.5. The ready-for-use hair coloring agent obtained is applied on a strand of hair and distributed uniformly with a brush. After a period of action of 30 minutes at 40° C., the hair is washed with a shampoo, subsequently rinsed with lukewarm water and then dried.

The colorings obtained are summarized in the following Table 3.

TABLE 1

Dyeing Results

| No. | a) Component (a), Containing Compound (I) or (II) / b) Aldehyde-containing Component (b) | | | Color Values Measured L | a | b |
|---|---|---|---|---|---|---|
| | | Color Shade After Dyeing | | | | |
| 1 | in (a) 1-ethyl-2-methyl-quinolinium iodide 3.45 g / in (b) 4-hydroxy-3-methoxy benzaldehyde 1.76 g | violet | untreated hair: after coloring: | +83.30 +27.79 | −0.48 +21.83 | +10.40 −9.62 |
| 2 | in a) 1-ethyl-2-methyl-quinolinium chloride 2.39 g / in b) 4-hydroxybenzaldehyde 1.43 g | red | untreated hair: after coloring: | +83.30 +39.72 | −0.48 +45.67 | +10.40 +10.77 |
| 3 | in a) 1-ethyl-2-methyl-quinolinium iodide 3.45 / in b) 3-hydroxy-4-methoxy-benzaldehyde 1.76 g / 2-amino-6-chloro-4-nitrophenol 0.05 g | yellow-orange | untreated hair: after coloring: | +83.30 +57.12 | −0.48 +22.39 | +10.40 +57.98 |
| | | Color shade after coloring | | | | |
| 4 | In a) 1-ethyl-2-methyl-quinolinium iodide 3.45 g / In b) 4-dimethylaminobenzaldehyde 1.72 g | rose-red | untreated hair: after coloring: | +83.30 +52.37 | −0.48 +45.55 | +10.40 +5.45 |
| 5 | in a) 1-ethyl-2-methyl-quinolinium chloride 2.39 g / in b) 3,4-dihydroxybenzaldehyde 1.59 g | black-violet | untreated hair: after coloring: | +83.30 +25.67 | −0.48 +6.94 | +10.40 −3.29 |
| 6 | in a) 1-ethyl-2-methyl-quinolinium chloride 2.39 g / in b) 3,5-dimethoxy-4-hydroxy-benzaldehyde 2.10 g | gasoline | untreated hair: after coloring: | +83.30 +27.34 | −0.48 +4.05 | +10.40 −9.12 |
| 7 | In (a) 1-ethyl-2-methyl-quinolinium chloride 2.39 g / In (b) 3,4,5-trihydroxybenzaldehyde monohydrate 1.98 g | brown | untreated hair: after coloring: | +83.30 +29.96 | −0.48 −5.49 | +10.40 +11.35 |
| 8 | In (a) 1-ethyl-2-methyl-quinolinium iodide 3.45 g / In (b) 3,5-dimethyl-4-hydroxy-benzaldehyde 1.98 g | blue-green | untreated hair: after coloring: | +83.30 +28.87 | −0.48 −2.76 | +10.40 −3.47 |
| 9 | in a) 1-ethyl-2-methyl-quinolinium chloride 2.39 g / in b) 3-ethoxy-4-hydroxybenzaldehyde 1.92 g | violet-black | untreated hair: after coloring: | +83.30 +34.19 | −0.48 +12.52 | +10.40 −5.77 |

TABLE 1-continued

Dyeing Results

| No. | a) Component (a), Containing Compound (I) or (II) b) Aldehyde-containing Component (b) | Color shade after coloring | | Color Values Measured L | a | b |
|---|---|---|---|---|---|---|
| 10 | in a) 1-ethyl-4-methyl-quinolinium iodide 3.45 g in b) 3-methoxy-4-hydroxybenzaldehyde 1.76 g | green | untreated hair: after coloring: | +83.30 +49.84 | −0.48 −8.42 | +10.40 +8.08 |

TABLE 2

Dyeing Results

| No. | c) Component (a), containing Compound (I) d) Aldehyde-containing Component (b) | Color shade after coloring | | Color Values Measured L | a | b |
|---|---|---|---|---|---|---|
| 11 | in (a) 1-ethyl-2-methyl-quinolinium iodide 3.45 g in (b) 4-hydroxy-3-methoxy benzaldehyde 1.76 g | violet | untreated hair: after coloring: | +83.30 +30.79 | −0.48 +4.44 | +10.40 −4.44 |
| 12 | in a) 1-ethyl-2-methyl-quinolinium chloride 2.39 g in b) 4-hydroxybenzaldehyde 1.43 g | red | untreated hair: after coloring: | +83.30 +37.84 | −0.48 +31.52 | +10.40 +16.55 |
| 13 | in a) 1-ethyl-2-methyl-quinolinium iodide 3.45 g in b) 3,5-dimethyl-4-hydroxybenzaldehyde 1.98 g | green | untreated hair: after coloring: | +83.30 +37.18 | −0.48 −3.47 | +10.40 −1.83 |

TABLE 3

Dyeing Results

| No. | e) Component (a), Containing Compound (II) f) Aldehyde-containing Component (b) | Color shade after coloring | | Color Values Measured L | a | b |
|---|---|---|---|---|---|---|
| 14 | in (a) 1-ethyl-2-methyl-quinolinium iodide 3.45 g in (b) 4-hydroxy-3-methoxy benzaldehyde 1.76 g | green | untreated hair: after coloring: | +83.30 +45.80 | −0.48 −6.22 | +10.40 +6.87 |
| 15 | in a) 1-ethyl-4-methyl-quinolinium chloride 2.39 g in b) 4-hydroxybenzaldehyde 1.43 g | brown | untreated hair: after coloring: | +83.30 +51.55 | −0.48 +4.68 | +10.40 +20.79 |
| 16 | in a) 1-ethyl-4-methyl-quinolinium iodide 3.45 g in b) 3,5-dimethyl-4-hydroxybenzaldehyde 1.98 g | green | untreated hair: after coloring: | +83.30 +45.71 | −0.48 −9.80 | +10.40 +17.79 |

The L*a*b color measurement values, given in the examples above, were measured with a Minolta, type Chromameter H colorimeter.

The L value here stands for the brightness (that is, a lower L value indicates a greater color intensity), while the "a" value is a measure of the red portion, that is, the higher "a" value varies indicates a greater proportion of red. The "b" value is a measure of the blue portion of the color, a more negative "b" value indicating a greater proportion of blue.

Unless stated otherwise, all percentages in the present application are percentages by weight.

What is claimed is:

1. An agent for coloring fibers, said agent containing an alkanolamine, at least one aromatic aldehyde compound and at least one quinolinium compound of formula (I) or (II),

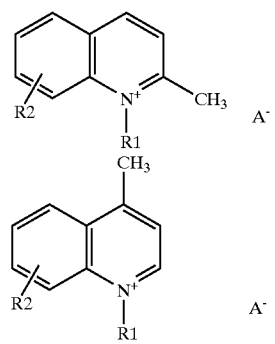

wherein R1 represents a C1 to C3 alkyl group, a C1 to C3 alkoxyalkyl group or a C1 to C3 hydroxyalkyl group and R2 represents hydrogen or a hydroxy group, a methoxy group, a halogen atom, an amino group or a dimethylamino group and A⁻ represents an anion.

2. The agent as defined in claim 1, obtained by mixing three components, wherein a first of the two components contains said at least one aromatic aldehyde compound and another of the two components contains said at least one quinolinium compound of the formula (I) or (II) and said alkanolamine.

3. The agent as defined in claim 1, obtained by mixing two components, wherein one of the two components contains said at least one aromatic aldehyde compound and said alkanolamine and another of the two components contains side at least one quinolinium compound of the formula (I) or (II).

4. The agent as defined in claim 1, obtained by mixing two components, wherein one of the two components contains said at least one aromatic aldehyde compound and said at least one quinolinium compound of the formula (I) or (II) and another of the two components contains said alkanolamine.

5. The agent as defined in claim 1, obtained by mixing two components, wherein a first of the three components contains said at least one quinoline compound of the formula (I) or (II), a second of the three components contains said at least one aromatic aldehyde compound and a third of the three components contains said alkanolamine.

6. The agent as defined in any one of claims 1 to 5, wherein the at least one quinoline compound of the formula (I) or (II) is selected from the group consisting of 1-ethyl-2-methyl-quinolinium iodide, 1-ethyl-2-methyl-quinolinium chloride, 1-ethyl-4-methyl-quinolinium iodide and 1-ethyl-4-methyl-quinolinium chloride.

7. The agent as defined in any one of claims 1 to 5, wherein said at least one aromatic aldehyde compound is selected from the group consisting of vanillin, isovanillin, 3,4-dihydroxybenzaldehyde, 4-hydroxy-benzaldehyde, 3,5, 4-dimethoxy--hydroxy-benzaldehyde, 4-dimethylamino-benzaldehyde, 4-dimethylamino-cinnamaldehyde, 4-hydroxy-2-methoxybenzaldehyde, 3,5-dimethyl-4-hydroxy-benzaldehyde, 4-dimethyl-amino-2-methoxybenzaldehyde, 2-hydroxy-benzaldehyde, 4-hydroxy-1-naphthaldeehyde, 4-dimethyl-amino-1-naphthaldehyde, 4'-hydroxybiphenyl-1-carbaldehyde, 4methoxy-1-nephthaldehyde, 2-hydroxy-3-methoxybenzaldehyde, 2,4-dihydroxybenzaldehyde, 3,4-dihydroxybenzaldehyde, 2,5-dihydroxy benzaldehyde, 2,3, 4-trihydroxy benzaldehyde, 3,4,5-trihydroxybenzaldehyde, 2,4,6-trihydroxybenzaldehyde, 2,4-dimethoxy-benzaldehyde, 2,3-dimethoxybenzaldehyde, 2,5-dimethoxybenzaldehyde, 3,5-dimethoxybenzaldehyde, 3,4-dimethoxybenzaldehyde, benzene-1,4-dicarbaldehyde, 4-ethoxy-benzaldehyde, 2-methyl-1,4-naphthoquinone, 4-carboxybenzaldehyde, 4-hydroxy-3-methoxycinnamaldehyde, 3,5-dimethoxy-4-hydroxycinnamaldehyde, 3-methoxy-4-(1-pyrrolidinyl)benzaldehyde, 4-diethylamino-3-methoxybenzaldehyde, 1,2-phthaldialdehyde, 4-dibutylamino-benzaldehyde, 4-diethylamino-2-hydroxy-benzaldelhyde, 3,4-dimethoxy-5-hydroxybenzaldehyde, 5(4-(diethylamino)phenyl)-2,4-pentadienal, 2-methoxy-1-naphthaldehyde, 3-ethoxy-4-hydroxybenzaldehyde, 2-nitrobenzaldehyde, 3-nitrobenzaldehyde and 4-nitrobenzaldehyde.

8. The agent as defined in any one of claims 1 to 5, wherein said at least one quinolinium compound of formula (I) or (II) and the at least one aldehyde compound are each present in an amount of 0.01 to 10 percent by weight.

9. The agent as defined in any one of claims 1 to 5, wherein said alkanolamine is monoethanolamine.

10. The agent as defined in any one of claims 1 to 5, wherein said anion is selected from the group consisting of chloride, bromide, iodide, sulfate, hydrogen sulfate, monomethyl sulfate, acetate and lactate.

11. The agent as defined in any one of claims 1 to 5, further comprising at least one direct dye compound.

12. The agent as defined in claim 3, wherein said another of the two components has a pH of 1.5 to 6.8 and said one of the two components has a pH of 9 to 13.

13. The agent as defined in any one of claims 1 to 5, having a pH of 3 to 11.

14. A method for coloring hair, said method comprising the steps of:

a) providing an agent for coloring the hair, said agent comprising containing an alkanolamine, at least one aromatic aldehyde compound and at least one quinolinium compound of formula (I) or (II):

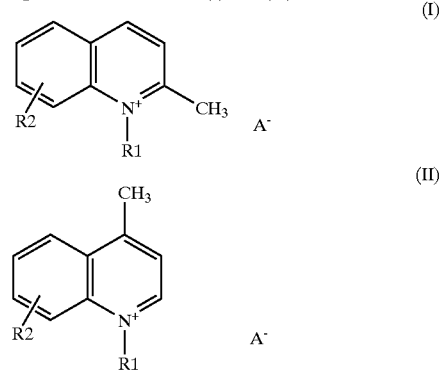

wherein R1 represents a C1 to C3 alkyl group, a C1 to C3 alkoxyalkyl group or a C1 to C3 hydroxyalkyl group and R2 represents hydrogen or a hydroxy group, a methoxy group, a halogen atom, an amino group or a dimethylamino group and A⁻ represents an anion;

b) applying the agent to the hair and allowing the agent to act on the hair for a period of 5 to 60 minutes at a temperature of 20° to 50° C.; and c) rinsing the hair with water and subsequently drying the hair.

15. The method as defined in claim 14, wherein said period is from 15 to 30 minutes and said temperature is from 30° to 40° C.

16. A multicomponent kit for coloring and later decolorizing fibers, wherein the kit contains a coloring agent and a decolorizing agent, said decolorizing agent having a pH of 4 to 8 and comprising at least one member selected from the group consisting of sulfites, hydrogen sulfites, thioglycolic acid and salts of thioglycolic acid; and wherein said coloring agent comprises an alkanolamine, at least one aromatic aldehyde compound and at least one quinolinium compound of formula (I) or (II):

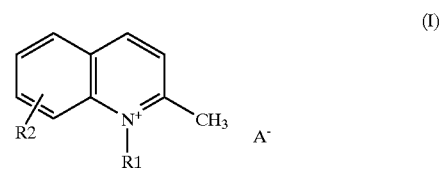

-continued
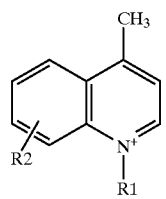
(II)
wherein R1 represents a C1 to C3 alkyl group, a C1 to C3 alkoxyalkyl group or a C1 to C3 hydroxyalkyl group and R2 represents hydrogen or a hydroxy group, a methoxy group, a halogen atom, an amino group or a dimethylamino group and A⁻ represents an anion.
* * * * *